(12) United States Patent
Sakaguchi et al.

(10) Patent No.: US 9,617,519 B2
(45) Date of Patent: Apr. 11, 2017

(54) METHOD FOR MANUFACTURING MULTILAYERED CELL SHEET, MULTILAYERED CELL SHEET HAVING VASCULAR NETWORK OBTAINED THEREBY, AND METHOD OF USE THEREOF

(75) Inventors: Katsuhisa Sakaguchi, Tokyo (JP); Tatsuya Shimizu, Tokyo (JP); Hidekazu Sekine, Tokyo (JP); Mitsuo Umezu, Tokyo (JP); Teruo Okano, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 13/823,007

(22) PCT Filed: Sep. 14, 2011

(86) PCT No.: PCT/JP2011/071056
§ 371 (c)(1),
(2), (4) Date: Mar. 13, 2013

(87) PCT Pub. No.: WO2012/036225
PCT Pub. Date: Mar. 22, 2012

(65) Prior Publication Data
US 2013/0173018 A1   Jul. 4, 2013

(30) Foreign Application Priority Data
Sep. 14, 2010  (JP) ................. 2010-225201

(51) Int. Cl.
| | | |
|---|---|---|
| *C12N 5/071* | (2010.01) | |
| *A61F 2/02* | (2006.01) | |
| *C12M 3/00* | (2006.01) | |
| *C12M 1/12* | (2006.01) | |
| *C12N 5/077* | (2010.01) | |

(52) U.S. Cl.
CPC .............. *C12N 5/0691* (2013.01); *A61F 2/02* (2013.01); *C12M 21/08* (2013.01); *C12M 25/02* (2013.01); *C12N 5/0657* (2013.01); *C12N 2502/28* (2013.01); *C12N 2513/00* (2013.01); *C12N 2533/54* (2013.01); *C12N 2533/56* (2013.01)

(58) Field of Classification Search
CPC ............................... C12N 5/0691; A61F 2/02
USPC .............. 623/23.72; 435/177, 182
See application file for complete search history.

(56) References Cited

U.S. PATENT DOCUMENTS

| | | | |
|---|---|---|---|
| 2004/0009566 A1 | 1/2004 | Okano et al. | |
| 2008/0131476 A1 | 6/2008 | Kanzaki et al. | |
| 2011/0269207 A1* | 11/2011 | Ringeisen | C12N 11/02 435/177 |

FOREIGN PATENT DOCUMENTS

| | | |
|---|---|---|
| JP | 2009-531067 A | 9/2009 |
| WO | 02/08387 A | 1/2002 |
| WO | 02/078439 A2 | 10/2002 |
| WO | 2010/065957 A2 | 6/2010 |
| WO | 2010/065957 A3 | 6/2010 |

OTHER PUBLICATIONS

Harimoto, Masami. Novel Approach for Achieving Double-Layered Cells Sheets co-culture: Overlaying Endothelial Cells Sheets onto Monolayer Hepatocytes Utilizing Temperature-Responsive Culture Dishes. 2002 Wiley Periodicals. pp. 464-470.*
Asakawa, Nahoko et al. Pre-Vascularization of in vitro Three-Dimensional Tissues Created by Cell Sheet Engineering. Biomaterials 31 (2010). pp. 3903-3909.*
Shimizu, Tatsuya et al. Polysurgery of cell sheet grafts overcomes diffusion limits to produce thick, vascularized myocardial tissues. The FASEB Journal Express. 2006. pp. 1-20.*
Lee, Kangwon et al. Growth factor delivery-based tissue engineering: general approaches and a review of recent developments. Journal of the Royal Society Interface. (2011) 8, pp. 153-170.*
Takei (Fabrication of Endothelialized Tube in Collagen Gel as Starting Point for Self-Developing Capillary-Like Network to Construct Three-Dimensional Organs In Vitro, 2006— filed on May 20, 2014).*
Asakawa (Pre-Vascularization of in vitro Three-Dimensional Tissues Created by Cell Sheet Engineering, 2010—filed on Jul. 30, 2013).*
Lee (Growth factor delivery-based tissue engineering: general approaches and a review of recent developments, 2010).*
International Search Report corresponding to PCT/JP2011/071055 mailed Nov. 15, 2011, 4 pages.
International Search Report corresponding to PCT/JP2011/071056 mailed Dec. 20, 2011, 3 pages.
Asakawa, Nahoko et al., "Pre-vascularization of in vitro three-dimensional tissues created by cell sheet engineering," *Proceedings of the Bioengineering Conference annual meeting of BE D/JSME* (Jan. 2010), vol. 22, p. 24.
Nagase, K. et al., "Temperature-responsive intelligent interfaces for bimolecular separation and cell sheet engineering," *J.R.Soc. Interface* (2009) 6(Suppl3), p. S293-309.

(Continued)

*Primary Examiner* — Scott Long
*Assistant Examiner* — Nghi Nguyen
(74) *Attorney, Agent, or Firm* — Kilpatrick Townsend & Stockton LLP (57) ABSTRACT

A method for manufacturing a multilayered cell sheet characterized in fabricating a vascular bed that constructs a vascular network extending to the surface from a channel for perfusing a medium, the channel being embedded in a gel; and layering a cell sheet onto the vascular bed to construct a vascular network in the cell sheet. This manufacturing method makes it possible to construct a vascular network in the cell sheet and to fabricate a thick multilayered cell sheet in a simple manner by layering cell sheets. Such a thick multilayered cell sheet is useful as an in-vivo tissue substitute in regenerative medicine involving a variety of tissues.

10 Claims, 6 Drawing Sheets

(56) References Cited

OTHER PUBLICATIONS

Noguchi, Shinsuke et al. "Fabrication of 3-dimensional tissue using human cells," *Dai 22 Kai Proceedings of the Bioengineering Conference annual meeting of BE D/JSME* (Jan. 2010), p. 24.

Noguchi, Shinsuke et al. "Kekkan Tsuki Sanjigen Soshiki Kochiku no Kento," *Regenerative Medicine* (2010), vo. 9, p. 176, 0-10-6.

Ogura, Shin'ya et al., "In vitro ni Okeru Kekkanmo Tsuki Hito Sanjigen Soshiki no Kochiku," *Regenerative Medicine* (Mar. 2011), vol. 10, p. 173, 0-23-6.

Sekiya, Sachiko et al., "Bioengineered cardiac cell sheet grafts have intrinsic angiogenic potential," *Biochem.Biophys.Res.Commun.*, (2006), 34:573-582.

Shimizu, Tatsuya. et al. "Polysurgery of cell sheet grafts overcomes diffusion limits to produce thick, vascularized myocardial tissues," *FASEB J.* (2006) 20:6:708-710 [online Jan. 26, 2006].

Shimizu, Tatsuya et al., "Fabrication of Pulsatile Cardiac Tissue Grafts Using a Novel 3-Dimensional Cell Sheet Manipulation Technique and Temperature-Responsive Cell Culture Surfaces," *Circulation Res.* (2002) vol. 90, p. e40-e48.

Sugibayashi, Ko et al. "Fabrication of three-dimensional tissues with vascular-like-cavity by sandwiching micropatterned hydrogel between two cell sheets," Institute of Advanced Biomedical Engineering and Science, Tokyo Women's Medical University, *Dai 31 Kai The Annual Meeting of the Japanese Society for Biomaterials Yokoshu* (2009), p. 236.

Sasagawa, Tadashi et al., "Design of prevascularized three-dimensional cell-dense tissues using a cell sheet stacking manipulation technology," *Biomaterials* (2010) 31:1646-1654.

EpigastaricFlap, Anatomy of Caudal area (2014).

Koning, Merel, "Current opportunities and challenges in skeletal muscle tissue engineering," *J Tissue Eng Regen Med* (2009) 3:407-415.

Masuda, Shinako et al., "Cell sheet engineering for heart tissue repair," *Advanced Drug Delivery Reviews* (2008) 60:277-285.

Matsuda, Noriaki et al., "Tissue Engineering Based on Cell Sheet Technology," *Adv. Mater.* (2007) 19:3089-3099.

Sekine, Hidekazu et al., "Pulsatile Myocardial Tubes Fabricatd With Cell Engineering," *Circulation* (2006) 114:1-87-1-93.

Sekine, Hidekazu et al., "Endothelial Cell Coculture Within Tissue-Engineered Cardiomyocyte Sheets Enhances Neovascularization and Improves Cardiac Function of Ischemic Hearts," *Circulation* (2008) 118:S145-S152.

Tanaka, M.D., Tanaka et al., "Tissue Engineering Skin Flaps: Which Vascular Carrier, Arteriovenous Shunt Loop or Arteriovenous Bundle, Has More Potential for Angiogenesis and Tissue Generation?" *Plastic and Reconstructive Surgery* (Nov. 2003) 112(6):1636-1644.

Todd, Brian A. et al., "Hydration Forces," Wiley Encyclopedia of Chemical Biology (2008) pp. 1-9.

Extended European Search Report corresponding to EP 11 82 5225 mailed Feb. 25, 2014, 7 pages.

Extended European Search Report corresponding to EP 11 82 5224 mailed Feb. 25, 2014, 6 pages.

Takei, Takayuki et al., "Fabrication of Endothelialized Tube in Collagen Gel as Starting Point for Self-Developing Capillary-Like Network to Construct Three-Dimensional Organs In Vitro," *Biotechnology and Bioengineering* (Sep. 5, 2009) 95(1):, 7 pages, Publication Date is Apr. 7, 2006.

\* cited by examiner

3sheets, 5 days 6 sheets, 10 days
(3 + 3 sheets)

9 sheets, 15days
(3 + 3 + 3 sheets)

12 sheets, 20days
(3 + 3 + 3 +3 sheets)

METHOD FOR MANUFACTURING MULTILAYERED CELL SHEET, MULTILAYERED CELL SHEET HAVING VASCULAR NETWORK OBTAINED THEREBY, AND METHOD OF USE THEREOF

TECHNICAL FIELD

The present invention relates to a method for producing a multilayered cell sheet useful in the field of medicine, biology, drug discovery, pharmacology, etc., a multilayered cell sheet having a vascular network obtained thereby, and a method of use thereof. The present application claims priority to a Japanese application (Japanese Patent Application No. 2010-225201) filed on Sep. 14, 2010.

BACKGROUND ART

Recently, animal cell culture techniques have been remarkably developed, and also research and development related to animal cells have been carried out in a wide variety of fields. In dealing with animal cells of interest, not only the originally developed animal cells per se as well as the products thereof have been commercialized, but the cells or their cell surface proteins have come to be analyzed to design useful pharmaceuticals, regenerate patient's cells in vitro, or return them after enhancing the function to the patient's body for therapy. At present, the technology of culturing, as well as evaluating, analyzing and using the animal cells are a field that are attracting researchers' attention. Many of the animal cells including human cells are attachment-dependent. Thus, when animal cells are intended to be cultured in vitro, first they must be attached to the surface of a substrate. Sometimes it is necessary to detach the cultured cells, without separating into pieces, while retaining the form as they are cultured on the surface of the substrate.

In particular, with regard to the technology of regenerating the patient's cells in vitro, organ transplantation which intends to replace the incurable organ with another person's organ has become popular in recent years. Targets include a wide variety of organs such as the skin, the cornea, the kidney, the liver, and the heart, and prognosis after surgery has become extremely well, indicating that the technology is being established as one medical technology. Take corneal transplant as an example. Eye Bank was established in Japan about 50 years ago, along with the start of transplantation activities. However, the number of donors is still small, and while patients who require corneal transplant is about 20,000 in Japan alone, the actual number of patients who can receive the transplantation is said to be one tenth, or about 2000. Despite that corneal transplantation is an mostly established technology, a further improved medical technology is being sought after, due to shortage of donors. Under these circumstances, a technique of culturing the patient's normal cells to the desired size for transplantation was developed.

Under these circumstances, Japanese Unexamined Patent Publication (Kokai) No. 02-211865 (Patent Document 1) discloses a novel method of culturing cells on a cell culture support, where the surface of the substrate is coated with a polymer having an upper or lower critical solution temperature of 0 to 80° C. in water, the cells are cultured at a temperature not exceeding the upper critical solution temperature or not falling below the lower critical solution temperature, and the cultured cells are detached by increasing or decreasing the temperature of the substrate to exceed the upper critical solution temperature or fall below the lower critical solution temperature, without treatment with an enzyme. Japanese Unexamined Patent Publication (Kokai) No. 05-192138 (Patent Document 2) also describes a method of culturing skin cells using this temperature-responsive cell culture substrate at a temperature not exceeding the upper critical solution temperature or not failing below the lower critical solution temperature and then detaching the cultured skin cells with low damage by increasing or decreasing the temperature of the substrate to exceed the upper critical solution temperature or fall below the lower critical solution temperature. Use of the temperature-responsive cell culture substrate has led to a variety of new developments on known, culture techniques. Furthermore, in Japanese Unexamined Patent Re-publication (Saikohyo) No. 02-008387 (Patent Document 3), it was found that by culturing myocardial cells on a cell culture support the surface of which being coated with a temperature-responsive polymer, obtaining a myocardial cell-like sheet, then allowing the cultured layered cell sheet to adhere to a polymer membrane at a medium temperature not exceeding the upper critical solution temperature or not falling below the lower critical solution temperature, detaching it as it is together with the polymer membrane, and changing it into a three dimensional structure by a given method, a cell sheet having few structural defects and several functions as a myocardium-like tissue in vitro and a three-dimensional structure can be obtained. However, With the conventional technology described above, the myocardium-like cell sheet cannot be infinitely layered, with about three layers being the limit, and thus there has been a strong need for a technology that easily permits layering for a plurality of times.

In order to resolve the above problems, FASEB, J., 20(6), 708-710 (2006) (Non-patent document 1) attempted to multilayer cell sheets in vivo, and obtained a multilayered myocardial sheet with a thickness of 1 mm. It was found that in order to obtain a thick multilayered cell sheet among them, nutrients and oxygen must be supplied to each multilayered cell and each cell sheet. However, in the method of FASEB. J., 20(6), 708-710 (2006) (Non-patent document 1), cell sheets must be repeatedly transplanted in vivo, and thus the implanted site must be opened each time, which poses a great burden to the recipient of the transplant. Thus, there has been a strong need for a technology that permits simple multilayering for a plurality of times.

Citation List

Patent Documents

Patent Document 1: Japanese Unexamined Patent Publication (Kokai) No. 02-211865
Patent Document 2: Japanese Unexamined Patent Publication (Kokai) No. 05-192138
Patent Document 3: Japanese Unexamined Patent Re-publication (Saikohyo) No. 02-008387

Non-Patent Documents

Non-patent document 1: FASEB. J., 20(6), 708-710 (2006)

SUMMARY OF THE INVENTION

Technical Problem

As described above, the present invention is intended to solve the problems on layering of cell sheet described, above. Thus, the present invention provides a novel method for producing a multilayered cell sheet developed based on a concept entirely different from the conventional art, a multilayered cell sheet having a vascular network obtained thereby, and a method for using it.

Solution to Problem

In order to solve the above problems, the present inventors have continued research from various viewpoints. As a result, it was found that by providing a channel in a gel for perfusing a medium, inducing vascular endothelial cells, fabricating a vascular bed having a vascular network constructed in the gel, and layering a cell sheet on the vascular bed, the vascular network can be constructed in the cell sheet, and cell sheets can be simply layered to a thick multilayer sheet. The present invention was made based on such a finding.

Thus, the present invention provides a method for producing a multilayered cell sheet, which comprises fabricating a vascular bed having a vascular network constructed from a channel provided in the gel for perfusing the medium to the surface, and layering a cell sheet on the vascular bed to construct a vascular network in the cell sheet. Furthermore, the present invention provides a multilayered cell sheet obtained thereby. The present invention further provides a method for using the multilayered cell sheet. The present invention is believed to be an extremely important invention that was realized for the first time using a cell structure based on an unprecedentedly novel concept that by using a vascular bed, a thick multilayered cell sheet can be fabricated in vitro.

Advantageous Effects of Invention

According to the production method of the present invention, a vascular network can be constructed in a cell sheet, and by layering the cell sheet, a thick multilayered cell sheet can be simply fabricated. Such a thick multilayered cell sheet is expected to be useful as an in-vivo tissue substitute in regenerative medicine for various tissues.

DESCRIPTION OF EMBODIMENTS

The purpose of the present invention is to fabricate a thick multilayered cell sheet in a simple manner. For that purpose, it is necessary to construct a vascular network in the multilayered cell sheet as described above. It was found in the present invention that by providing a channel in the gel and perfusing a medium to the channel, a vascular network can be simply formed between the channel in the gel and the surface. In one such technology, for example, a cell sheet containing vascular endothelial cells is allowed to adhere to the gel surface, and to perfuse a medium to the channel in the gel, so that vascular endothelial cells in the cell sheet are arranged in the gel toward the channel, resulting in the construction of a vascular network in the gel. As other technologies, there can be mentioned one in which by suspending vascular endothelial cells in a medium to be perfused to the channel in the gel, a vascular network can be constructed in between the channel in the gel and the surface. When a channel is to be provided in the gel, it is only required to create a region in which no gel has been filled, and any material can be used for that purpose without limitation. For example, there can be used, but not limited to, stainless steel wire, silicone wire, a metal, a polymer and the like.

The vascular bed refers to a structure that is found in a biological tissue and organ and that has combined capillary vessels and peripheral tissues. The vascular bed plays a function of exchanging oxygen, glucose and other nutrients in the biological tissue via thin walls of capillary vessels that run throughout the vascular bed. Waste products such as carbon dioxide are exudated into the capillary vessels in the vascular bed. It is because of this material exchange that tissue fluids in the biological tissues are maintained at relatively constant levels. As used herein, a vascular bed that performs the function of efficiently exchanging oxygen, glucose and other nutrients in the cell sheet was artificially fabricated in vitro and used.

When a vascular bed having a channel for perfusing a medium, etc., into the gel is fabricated, the gel may be mixed with the cells before fabrication. At this time, the cell type to be mixed with the gel, the number of cells, the ratio, etc., are not limited, and may be selected or adjusted as appropriate depending on the biological tissue to be transplanted, the organ, the site, use, etc. For example, when the object is the regeneration of the myocardial tissue or a method for evaluating the myocardial function, cells used include one type or combinations of two types or more of myocardial cells, cardiac myoblasts, myoblasts, mesenchymal stem cells, vascular endothelial, cells, vascular endothelial progenitor cells, fibroblasts, bone marrow-derived cells, and adipose-derived cells, and their types are not limited in any way. When the object is the regeneration of the liver tissue, the generation of an artificial liver simulating the liver tissue or a method for evaluating the function of the liver tissue, cells that can be used include, for example, one type or combinations of two types or more of hepatic parenchymal cells, sinusoidal endothelial cells, Kupffer cells, stellate cells, pit cells, biliary epithelial cells, vascular endothelial cells, vascular endothelial progenitor cells, fibroblasts, bone marrow-derived cells, adipose-derived cells, and mesenchymal stem cells, and their types are not limited in any way. When the object is the regeneration of the renal tissue, the generation of an artificial kidney simulating the renal tissue or a method for evaluating the renal function, cells that can be used include, for example, one type or combinations of two types or more of kidney cells, granular cells, collecting duct epithelial cells, parietal epithelial cells, podocytes, mesangial cells, smooth muscle cells, renal, tubular cells, interstitial cells, glomerular cells, vascular endothelial cells, vascular endothelial progenitor cells, fibroblasts, bone marrow-derived cells, adipose-derived cells, and mesenchymal stem cells, and their types are not limited in any way. When the object is the regeneration of the adrenal tissue, the generation of an artificial adrenal gland simulating the adrenal gland or a method for evaluating the adrenal function, cells that can be used include, for example, one type or combinations of two types or more of adrenomedullary cells, adrenal cortical cells, spherical layer cells, zonal fasciculate cells, network layer cells, vascular endothelial cells, vascular endothelial progenitor cells, fibroblasts, bone marrow-derived cells, adipose-derived cells, and mesenchymal stem cells, and their types are not limited in any way. When the object is the regeneration of the skin or a method for evaluating the skin function, cells that can be used include, for example, one type or combinations of two types or more of epidermal keratinocytes, melanocytes, piloeraction muscle cells, hair follicle cells, vascular endothelial cells, vascular endothelial progenitor cells, fibroblasts, bone marrow-derived cells, adipose-derived cells, and mesenchymal stem cells, and their types are not limited in any way. When the object is the regeneration of the mucosal tissue or a method for evaluating the mucosal tissue function, for example, cells that can be used include cells harvested from tissues constituting the mucus. As the type of the mucous membrane, there can be mentioned buccal mucosa, gastric mucosa, intestinal mucosa, olfactory epithelium, oral mucosa, uterine mucous membrane, and the like. Among the cells harvested from the mucous tissue, one type or combinations of two types or more of the cells can be mentioned, and their types are not limited in any way.

Though the gel as used herein is not specifically limited, a gel comprising a biodegradable polymer is most suitable when the object is the use of a multilayered cell sheet obtained in transplant treatment into a living body. In that case, the biodegradable polymer part disappears in vivo, and the multilayered cell sheet of the present invention comes to be conjugated to the living body via blood vessels. The type of such biodegradable polymers includes, but not limited to, one type or combinations of two types or more of collagen, fibrin, gelatin, polysaccharide, elastin, fibronectin, laminin, chitin, chitosan and the like.

The present invention intends to use a gel having a vascular network thus obtained and to construct a vascular network in a cell sheet engrafted as a vascular bed on the gel. Thus, the present invention provides a technology for constructing a vascular network in a cell sheet by using an artificial product of a gel. At this time, while those circulated in the vascular bed may be, but not limited to, any of a culture medium, blood, serum, etc., there can be mentioned a culture medium as one that is easy to handle. While the type of the medium is not specifically limited, it may preferably be suitable for the cells constituting the cell sheet to be cultured on the vascular bed. For example, when a cell sheet consisting of myocardial cells is layered on the vascular bed, the M199 medium for culturing myocardial cells may be preferred.

The type of the cells to be used in the cell sheet of the present invention is not specifically limited, and cells of the site of interest to be transplanted using the multilayered cell sheet obtained, or cells derived from the desired organ or tissue to be evaluated may be used. For example, when the object is the regeneration of the myocardial tissue or a method for evaluating the myocardial function, cells used include one type or combinations of two types or more of myocardial cells, cardiac myoblasts, myoblasts, mesenchymal stem cells, vascular endothelial cells, vascular endothelial progenitor cells, fibroblasts, bone marrow-derived cells, and adipose-derived cells, and their types are not limited in any way. When the object is the regeneration of the liver tissue, the generation of an artificial liver simulating the liver tissue or a method for evaluating the function of the liver tissue, cells that can be used include, for example, one type or combinations of two types or more of hepatic parenchymal cells, sinusoidal endothelial cells, Kupffer cells, stellate cells, pit cells, biliary epithelial cells, vascular endothelial cells, vascular endothelial progenitor cells, fibroblasts, bone marrow-derived cells, adipose-derived cells, and mesenchymal stem cells, and their types are not limited in any way. When the object is the regeneration of the renal tissue, the generation of an artificial kidney simulating the renal tissue or a method for evaluating the renal function, cells that can be used include, for example, one type or combinations of two types or more of kidney cells, granular cells, collecting duct epithelial cells, parietal epithelial cells, podocytes, mesangial cells, smooth muscle cells, renal tubular cells, interstitial cells, glomerular cells, vascular endothelial cells, vascular endothelial progenitor cells, fibroblasts, bone marrow-derived cells, adipose-derived cells, and mesenchymal stem cells, and their types are not limited in any way. When the object is the regeneration of the adrenal tissue, the generation of an artificial adrenal gland simulating the adrenal gland or a method for evaluating the adrenal function, cells that can be used include, for example, one type or combinations of two types or more of adrenomedullary cells, adrenal cortical cells, spherical layer cells, zonal fasciculate cells, network layer cells, vascular endothelial cells, vascular endothelial progenitor cells, fibroblasts, bone marrow-derived cells, adipose-derived cells, and mesenchymal stem cells, and their types are not limited in any way. When the object is the regeneration of the skin or a method for evaluating the skin function, cells that can be used include, for example, one type or combinations of two types or more of epidermal keratinocytes, melanocytes, piloeraction muscle cells, hair follicle cells, vascular endothelial cells, vascular endothelial progenitor cells, fibroblasts, bone marrow-derived cells, adipose-derived cells, and mesenchymal stem cells, and their types are not limited in any way. When the object is the regeneration of the mucosal tissue or a method for evaluating the mucosal tissue function, for example, cells that can be used include buccal mucosa, gastric mucosa, intestinal mucosa, olfactory epithelium, oral mucosa, uterine mucous membrane, and the like. Among the cells harvested from the mucous tissue, one type or combinations of two types or more of the cells can be mentioned, and their types are not limited in any way.

The content ratio of the above cells is not specifically limited. At this time, if the cell sheet contains vascular endothelial cells, vascular endothelial, progenitor cells, etc., the vascular network could be conveniently constructed in the cell sheet in an efficient manner.

Cells as used herein include, but not limited to, cells directly harvested from biological tissues, cells directly harvested and differentiated in an culture system, or cell lines. While the origin of these cells is not specifically limited, there can be mentioned, for example, humans, rats, mice, guinea pigs, marmosets, rabbits, dogs, cats, sheep, pigs, goats, monkeys, chimpanzees, or immunodeficient animals thereof. When the multilayered cell sheet of the present invention is used in treating a human subject, cells derived from humans, pigs, monkeys, or chimpanzees may preferably be used.

While cells as used herein are not specifically limited, they may be cells fluorescently or chromogenically stained using at least one method with a reagent, a protein, a gene, etc. When reporter gene-introduced cells are used, the activity of a cell sheet or a multilayered cell sheet can be known by detecting fluorescence derived from a reporter protein obtained by the expression of a reporter gene, or fluorescence emitted by the reaction of a reporter protein and a specific substrate thereof. The reporter gene or reporter protein used include, but not limited to, for example, green fluorescent protein (GFP), chloramphenicol acetyltransferase (CAT), DsReD, β-glucronidase, LacZ, Kaede, luciferase, alkaline phosphatase and the like. A method for introducing a gene into the cell may be any conventional method, and include, but not limited to, for example, a lipofection method, a viral vector method, a calcium phosphate method, an electroporation method, a DEAE dextran method, and a microinjection method. Cells derived from a gene-transduced animal (transgenic animal) in which a reporter gene has been introduced into the host's genome using these gene transduction methods may be used. The promoter sequence controlling the expression of the reporter gene is not specifically limited, and may be selected as appropriate depending on the purpose of detecting the expression of the reporter gene.

The cell sheet of the present invention can be obtained by culturing cells at a temperature zone in which the hydration force of a polymer, of which hydration force varies in the temperature range of 0-80° C., is weak on a cell culture support the surface of which is coated with the polymer, and then detaching the cultured cells in a sheet form by varying the temperature of the culture medium to a temperature in which the hydration force of the polymer is strong. At this time, the cells may be cultured at a temperature zone in which the hydration force of a polymer, of which hydration force varies in the temperature range of 0-80° C., is weak on a cell culture support the surface of which is coated with the polymer. Usually, the temperature may preferably be 37° C. which is a temperature for culturing cells. The temperature-responsive polymer for use in the present invention may be any of a homopolymer or copolymer. As such polymers, there can be mentioned polymers described in Japanese Unexamined Patent Publication (Kokai) No. 2-211865. Specifically, it can be obtained by monopolymerization or copolymerization of the following monomers. Monomers that can be used include, for example, a (meth)acrylamide compound, a N- (or N,N-di) alkyl-substituted (meth)acrylamide derivative, or a vinylether derivative, and in the case of a copolymer, any two or more of these can be used. Furthermore, a copolymer with monomers other than the above monomers, a graft polymer or copolymer with each other, or a mixture of polymers and copolymers can be used. Also, crosslinking can be performed as long as it does not impair the inherent property of the polymer. Since cells are cultured and detached at this time, and separation is carried out in the range of 5° C. to 50° C., temperature-responsive polymers include, but not limited to, poly-N-n-propyl acrylamide (the lower critical dissolution temperature of the monomer alone is 21° C.), poly-N-n-propyl methacrylamide (the lower critical dissolution temperature of the monomer alone is 27° C.), poly-N-isopropyl acrylamide (the lower critical dissolution temperature of the monomer alone is 32° C.), poly-N-isopropyl methacrylamide (the lower critical dissolution temperature of the monomer alone is 43° C.), poly-N-cyclopropyl acrylamide (the lower critical dissolution temperature of the monomer alone is 45° C.), poly-N-ethoxyethyl acrylamide (the lower critical dissolution temperature of the monomer alone is 35° C.), poly-N-ethoxyethyl methacrylamide (the lower critical dissolution temperature of the monomer alone is 45° C.), poly-N-tetrahydrofurfuryl acrylamide (the lower critical dissolution temperature of the monomer alone is 28° C.), poly-N-tetrahydrofurfuryl methacrylamide (the lower critical dissolution temperature of the monomer alone is 35° C.), poly-N,N-ethylmethyl acrylamide (the lower critical, dissolution temperature of the monomer alone is 56° C.), poly-N,N-diethyl acrylamide (the lower critical dissolution temperature of the monomer alone is 32° C.), and the like. Monomers as used herein for copolymerization include, but not limited to, polyacrylamide, poly-N,N-diethyl acrylamide, poly-N,N-dimethyl acrylamide, polyethylene oxide, polyacrylic acid and a salt thereof, hydrated polymers such as polyhydroxyethyl methacrylate, polyhydroxyethyl acrylate, polyvinyl alcohol, polyvinyl pyrrolidone, cellulose, and carboxymethyl cellulose.

A method of coating the surface of the substrate with each of the above polymer as used herein include, but not limited to, subjecting the substrate and the above monomer or polymer to an electron beam irradiation (EB), gamma-ray irradiation, ultraviolet ray irradiation, plasma treatment, corona treatment, and an organic polymerization reaction, or physical adsorption such as coating and kneading. The amount coated of a temperature-responsive polymer on the surface of the culture substrate may be in the range of 1.1-2.3 µg/cm$^2$, preferably 1.4-1.9 µg/cm$^2$, and more preferably 1.5-1.8 µg/cm$^2$. If the amount of coating is less than 1.1 µg/cm$^2$, the cells on the polymer cannot be easily detached even if stimulated, and inconveniently deteriorates work efficiency. Conversely, if the amount of coating exceeds 2.3 µg/cm$^2$, the cells cannot easily attach to the region, and thus the cells cannot be fully attached. In such a case, if a cell-adhering protein is further coated on the temperature-responsive polymer coating layer, the amount of the temperature-responsive polymer coating on the substrate surface may be 2.3 µg/cm$^2$ or more, and the amount coated of the temperature-responsive polymer may preferably be 9.0 µg/cm$^2$ or less, preferably 8.0 µg/cm$^2$ or less, and suitably 7.0 µg/cm$^2$ or less. When the amount coated of the temperature-responsive polymer is 9.0 µg/cm$^2$ or more, it makes the attachment of cells difficult even if a cell-adhering protein is further coated on the temperature-responsive polymer coating layer, and thus is not desirable. The type of such a cell-adhering protein includes, but not limited to, one type or a mixture of two types or more of, for example, collagen, laminin, laminin 5, fibronectin, matrigel, etc. The method for coating these cell-adhering proteins may follow any standard method, and usually a method of applying an aqueous solution of a cell-adhering protein to the substrate surface, and then removing the aqueous solution and rinsing is used. The present invention is a technology of using the cell sheet per se as much as possible using a temperature-responsive culture dish. Thus, an extremely large amount of a cell-adhering protein coated on the temperature-responsive polymer is not preferred. The measurement of the amount coated of a temperature-responsive polymer and the amount coated of a cell-attaching protein may follow any standard method, and there can be mentioned a method of measuring directly the cell-attached part using FT-IR-ATR, and a method of immobilizing a previously labelled polymer in a similar method and then estimating from the amount of the labelled polymer immobilized to the cell-attachment part, and any of the two methods can be used.

According to the method of the present invention, the number of cells inoculated at the time of culturing may vary depending on the animal species used, but may generally be $0.4 \times 10^6$ to $2.5 \times 10^6$ cells/cm$^2$, preferably $0.5 \times 10^6$ to $2.1 \times 10^6$ cells/cm$^2$, and more preferably $0.6 \times 10^6$ to $1.7 \times 10^6$ cells/cm$^2$, when the inoculum concentration is $0.4 \times 10^6$ cell/cm$^2$ or less, generally cells do not grow properly, the function of the cell sheet obtained cannot be expressed properly, and thus is not preferred in working the present invention. As used herein, in order to detach and recover the cultured cell sheet from the temperature-sensitive substrate, the temperature of the culture substrate to which the cultured cells are attached can be varied to higher than the upper critical dissolution temperature or lower than the lower critical dissolution temperature of the coating polymer on the culture substrate for detaching. At this time, this can be performed in the culture medium or in another isotonic solution, which can be selected depending on the purpose. In order to detach and recover more quickly and more efficiently, there can be used a method of lightly tapping or shaking the substrate and furthermore a method of stirring the culture medium using a pipet, alone or in combination. The culture conditions other than the temperature may follow any standard method, and is not specifically limited. For example, the medium used may be one to which a known serum such as fetal calf serum (FCS) has been added or a serum-free medium that contains no such serum.

The above will now be explained by taking poly (N-isopropylacrylamide) as an example of a temperature-responsive polymer. Poly (N-isopropylacrylamide) is known to be a polymer having a lower critical dissolution temperature of 31° C. Therefore, in a free state, the polymer chain dehydrates at a temperature of 31° C. or higher in water, thereby aggregating and becoming cloudy. Conversely, at a temperature of 31° C. or lower, the polymer chain hydrates and becomes dissolved in water. According to the present invention, this polymer has been coated and immobilized on the surface of the substrate such as a petri dish. Thus, at a temperature of 31° C. or higher, the polymer on the substrate surface may dehydrate, but since the polymer chain is coated and immobilized on the substrate surface, the substrate surface comes to exhibit hydrophobicity. Conversely, at a temperature of 31° C. or lower, the polymer on the substrate surface may hydrate, but since the polymer chain is coated and immobilized on the substrate surface, the substrate surface comes to exhibit hydrophilicity. The hydrophobic surface at this time is the surface suitable for cell's attachment and growth, and the hydrophilic surface becomes a surface to which cells cannot attach, and thus the cells in culture or the cell sheet can be easily detached only by cooling.

As a substrate that is coated, those commonly used in cell culture such as glass, reformed glass, polystyrene, a compound such as polymethylmethacrylate may be used, and a substance that can be shaped such as a polymer compound other than the above and ceramics can be used.

The shape of the culture substrate for use in the present invention is not specifically limited, and, for example, a dish, a multiplate, a flask, a cell insert cultured on a porous membrane, or a flat membrane may be mentioned. As a substrate that is coated, those commonly used in cell culture such as glass, reformed glass, polystyrene, a compound such as polymethylmethacrylate, and a substance that can be shaped such as a polymer compound other than the above and ceramics can be used.

The cell sheet for use in the present invention is free of damage by proteolytic enzymes as represented by dispase and trypsin during culture. Thus, the cell sheet detached from the substrate has an adhesive protein, and when the cells are detached in a sheet form, the cell-cell desmosome structure can be maintained to a certain degree. This permits a favorable adhesion to the vascular bed when placed thereon, and permits an efficient engraftment. For dispase that is a proteolytic enzyme, it is generally known that a cell-cell desmosome structure can be detached while maintaining it for 10-40%. However, since most of the basal membrane-like proteins in between the cell-substrate are destroyed, the cell sheet obtained has a weak strength. In contrast, the cell sheet of the present invention maintains 60% or more of both of the desmosome structure and the basal membrane-like protein, and thus various effects mentioned above can be obtained.

A method for fabricating a multilayered cell sheet of the present invention is not specifically limited, and the multilayered cell sheet can be obtained by detaching the cultured cells in a sheet-like form and layering the cultured cell sheets with each other using, as needed, a device for moving cultured cells. At this time, the temperature of the culture medium is not specifically limited, as long as it is lower than the upper critical dissolution temperature when the polymer coated on the surface of the culture substrate has the temperature, or higher than the temperature of the lower critical dissolution temperature when the polymer has the temperature. However, it is needless to say that a low temperature range in which cultured cells cannot grow or a high temperature range in which cultured cells die is obviously not suitable for culturing. Culture conditions other than the temperature may follow any standard method, and is not specifically limited. For example, the medium used may be one to which a known serum such as fetal calf serum (FCS) has been added or a serum-free medium that contains no such serum. Also, as needed, a device for moving a cell sheet can be used. Such a device is not specifically limited with regard to the material or shape, as long as it can capture the detached cell sheet. As such a material, generally, a material such as polyvinylidene difluoride (PVDF), silicone, polyvinyl alcohol, urethane, cellulose and a derivative thereof, chitin, chitosan, collagen, gelatin, or fibrin glue may be used in the form of a membrane, a porous membrane, an nonwoven fabric, or a woven fabric by being contacted with the cell sheet.

Thus, in accordance with the present invention, a thick multilayered cell sheet can be obtained. When a vascular network as in the present invention was not constructed, three layers was the most in which the multilayered cell sheet could survive. According to the present invention, cell sheets of four layers or more can be layered. At this time, the layering method is not specifically limited, but layering cell sheets of 3 layers or less for a plurality of times may be preferred to layering the cell sheet at one time. Also, the timing of layering may preferably be when a vascular network connected to the vascular bed has been fully constructed. The number of layering times may be appropriately matched with the purpose of use of the multilayered cell sheet, and may preferably be, but not limited to, 5 layers or more, more preferably 10 layers or more, and still more preferably 15 layers or more. When the thickness of the multilayered cell sheet is increased, the effects of the present invention can be markedly received, and a larger amount of cells an be conveniently transplanted to the transplant recipient.

In accordance with the present invention, by layering the upper surfaces of two cell sheets with each other, a structure having a channel on both of the upper surface and the lower surface of the multilayered cell sheet can be obtained, and by connecting the channels to a living body, nutrients and oxygen can be efficiently introduced into the multilayered cell sheet.

In another method, by layering a gel having a channel provided therein on a cell sheet that was layered on the vascular bed, a structure having a channel on both of the upper surface and the lower surface of the multilayered cell sheet can be obtained. The multilayered cell sheet fabricated has a channel of a blood vessel-like structure connected to the inside of the cell sheet on both of the upper surface and the lower surface of the multilayered cell sheet. By connecting the channel to the blood vessel of the living body, nutrients and oxygen can be efficiently introduced into the multilayered cell sheet.

In accordance with the present invention, the method for constructing the vascular network is not specifically limited. At this time, the flow rate of the culture medium perfused in the gel is not specifically limited, and the maximum flow rate may preferably be the largest flow rate at which the channel in the gel is not destroyed, and the minimum flow rate may preferably be the smallest flow rate at which the culture medium can reach the gel surface. The numerical values cannot be specifically indicated since it is greatly influenced by such factors as the size of the channel and the property of the gel.

When a multilayered cell sheet having a channel on both of the upper surface and the lower surface is fabricated by layering a gel having a channel provided therein on a cell sheet layered on the vascular bed, the flow rate of the culture medium may be varied for perfusion in the upper and lower channels of the multilayered cell sheet. When perfusion culture was performed by using different flow rates of the culture medium at the upper and lower channels of the multilayered cell sheet, a phenomenon in which vascular endothelial cells migrate toward the channel in which the culture medium is perfused faster can be seen. Thus, since the migration of vascular endothelial cells is promoted, a multilayered cell, sheet having a mature capillary vascular network can be obtained. In order to allow vascular endothelial cells to migrate into both of the upper and lower channels of the multilayered cell sheet, a method of switching the flow rate of the upper channel and the flow rate of the lower channel with each other of the culture medium perfused at a constant time interval can be used.

The temperature, humidify, and atmosphere in the perfusion culture of a multilayered cell sheet may follow a standard cell culture method, and is not specifically limited. At this time, the culturing method may be one that comprises culturing the multilayered cell sheet layered on the vascular bed by perfusing a culture medium from a channel formed in the gel of the vascular bed, one that comprises culturing by immersing the multilayered cell sheet in a culture medium filled in a sealed container that can maintain a constant temperature, humidity, and atmosphere, or one that comprises culturing by perfusing a culture medium from the channel formed in the gel in the vascular bed while being immersed in the culture medium. Culturing by perfusing the culture medium from the channel formed in the gel in the vascular bed while being immersed in the culture medium can promote vascular formation in the vascular bed and vascular formation in the multilayered cell sheet, and thus may be preferred.

Culturing the multilayered cell sheet layered on the vascular bed while applying pressure to a sealed container that can maintain a constant temperature, humidity, and atmosphere can increase the concentration of dissolved oxygen in the culture medium and can promote vascular formation, and thus may be preferred. The strength of pressure may be optimized as appropriate, since it is greatly influenced by a variety of factors depending on the size of the container, the size of the multilayered cell sheet to be cultured, and the amount of the culture medium. As used herein, it may be 5 mmHg or more, preferably 10 mmHg or more, and most preferably 15 mmHg or more.

As a method of promoting construction of a capillary vascular network in the multilayered cell sheet and in between the multilayered cell sheet and the vascular bed, there can be mentioned a method of adding a factor that promotes neovascular formation to a culture medium to be perfused to the vascular bed, or a culture medium for immersing the entire vascular bed, or in both of the culture media. A factor to be added herein may be any factor that induces neovascular formation, and is not specifically limited. There can be mentioned, for example, vascular endothelial growth factor (VEGF), hepatocyte growth factor (HGF), fibroblast growth factor (FGF), epidermal growth factor (EGF), platelet-derived growth factor (PDGF), insulin-like growth factor (IGF), angiopoietin, transforming growth factor-$\beta$ (TGF-$\beta$), placental growth factor (PlGF), MMP, family proteins of the above-mentioned factors, or the like. One or combinations of two or more of the above may be selected as a factor to be added to the culture medium for promoting neovascular formation. The concentration of a neovascular formation-promoting factor to be added to the culture medium may be optimized as appropriate, since it is greatly influenced by a variety of factors such as the type and number of cells included in the cell sheet, the size of the cell sheet, and the type of the vascular bed, and cannot be specifically described herein.

The temperature, humidity, and atmosphere during the perfusion culture of a multilayered cell sheet may follow a standard cell culture method used, and is not specifically limited. At this time, the multilayered cell sheet may be cultured by perfusing the culture medium from a channel formed in the gel in the vascular bed, or may be cultured by immersing the multilayered cell sheet in a culture medium filled in a sealed container that can maintain a constant temperature, humidity, and atmosphere. The most preferred method is culturing by perfusing a culture medium from a channel formed in the gel in the vascular bed, while immersing the multilayered cell sheet in a culture container filled with a culture medium in a sealed container that can maintain a constant temperature, humidity, and atmosphere.

As a method of constructing a mature vascular network in the multilayered cell sheet prepared according to the present invention, there can be mentioned a method of detaching a multilayered cell sheet layered on the vascular bed made of the gel from the vascular bed, and retransplanting on a vascular bed derived from a biological tissue segment removed from a living body of an animal including a human, or on an artificial vascular bed equipped with a flap or an artery and a vein. A vascular bed derived from a biological tissue and an artificial vascular bed equipped with a flap or an artery and a vein derived from a biological tissue segment retains an artery and a vein derived from a living body, and since the multilayered cell sheet obtained according to the present invention is connected to the capillary vascular network via these arteries and veins, a multilayered cell sheet capable of being transplanted to a given site in a living body can be obtained. While a method for preparing a vascular bed derived from a living body is not specifically limited, there can be mentioned a method in which a biological tissue segment to which an artery and a vein is connected is excised with an electric knife to create a state in which one each of an artery and a vein is connected to the biological tissue segment, and while maintaining the state, it is retained in the living body for about one week. An artificial vascular bed refers to a vascular bed-like structure in which a capillary vascular network has been constructed and the gel and/or cells have been filled in the interstatium of the capillary vascular network. While a method of fabricating an artificial vascular bed is not specifically limited, there can be mentioned a method in which an artery-vein loop in which an artery and a vein in the living body has been anastomosed is included in a region partitioned in a sterile container, and filling the gel in the partitioned region, which is dwelled in the living body to construct a capillary vascular network. Cells contained in the artificial vascular bed are not specifically limited, and may be selected as appropriate depending on the site to be transplanted and the use thereof.

A multilayered cell sheet obtained according to the present invention can be transplanted to a given site of a living body. The method includes, but not limited to, a method of connecting a channel provided in the multilayered cell sheet of the present invention and the blood vessel of a living body and a method of allowing the surface of a multilayered cell sheet to attach to a living body, whereupon blood vessel induction may have been carried out in advance at the transplanted site, and is not specifically limited. As used herein, a method of inducing blood vessels includes, but not limited to, for example, a method of embedding FGF, a blood vessel growth factor, into microspheres, and allowing it to act on a living body for 8-10 days while varying the composition, site, and injection range of the microspheres, a method of cutting a polyethylene terephthalate mesh into an arbitrary size, preparing a bag-like product, placing FGF dissolved in a high concentration agarose solution in the bag, and removing the bag 8-10 days later to fabricate a space in which blood vessels were induced, and the like.

When the multilayered cell sheet of the present invention is used on a human, the transplanted multilayered cell sheet can express its function in a human body for a long time. The amount expressed can be controlled by the size and shape of the detached multilayered cell sheet, or by both of them. If the constituent cells of such a multilayered cell sheet are myocardial cells, cardiac myoblasts, myoblasts, or mesenchymal stem cells, it can be used for the purpose of treating diseases accompanied by a disease or disorder selected from the group consisting of cardiac failure, ischemic heart disease, myocardial infarction, myocardial disease, myocarditis, hypertrophic cardiomyopathy, dilated phase of hypertrophic cardiomyopathy, and dilated cardiomyopathy, but the transplant recipient may be identified, as appropriate, depending on the cell type used, and is not specifically limited.

If the cell sheet or the present invention or a three dimensional structure can be transplanted to animals, they would be animals for evaluating pharmaceuticals. And the amount expressed of function can be controlled in the size and shape of the detached multilayered cell sheet. Animals used herein include, but not limited no, rats, mice, guinea pigs, marmosets, rabbits, dogs, pigs, chimpanzees, or immunodeficient animals thereof. For example, such animals may be used in, but not limited to, a system for evaluating cardiac function in which a test substance can be administered to these animals to judge the effect of the test substance on the cardiac function.

EXAMPLES

While the present invention will now be explained in detail with reference to specific examples, if should be noted that the present invention is not limited to them in any way.

Example 1

Method for Preparing Myocardial Cell Sheet

In this experiment, myocardial cells isolated from the heart of SD rats on day 0 after birth and cultured were used. After removing the heart from a rat pup, myocardial cells were isolated using collagenase Type II (manufactured by Worthington), an enzyme that decomposes collagen which is a major tissue component. The isolated myocardial cells were inoculated at a concentration of $320 \times 10^4$ cells/dish to a temperature-responsive culture dish ($\phi$35 mm, Dish Upcell Type-E manufactured by CellSeed). Four days later when the myocardial cells reached confluence on the surface of the culture dish, the temperature was reduced to 20° C. to recover the sheet-like myocardial cell groups. In this experiment, the tissue layered in 3 layers by pipetting was used.

(Method for Preparing a Gel Having a Channel Provided Therein)

Figure 1:
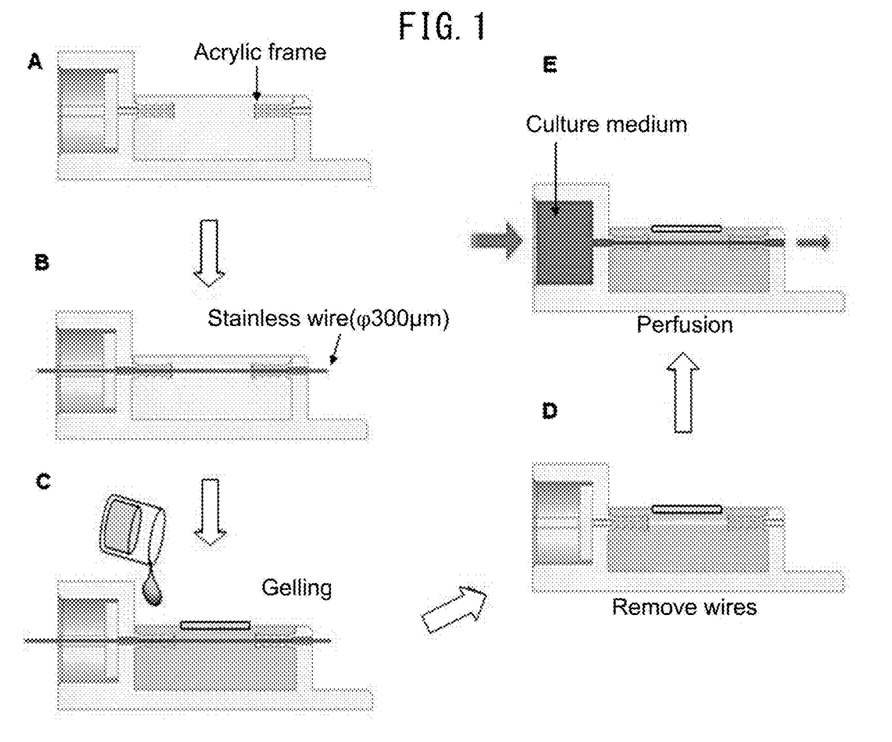
FIG. 1 is a diagram showing the outline of a procedure for fabricating the vascular bed of Example 1.
Figure 2:
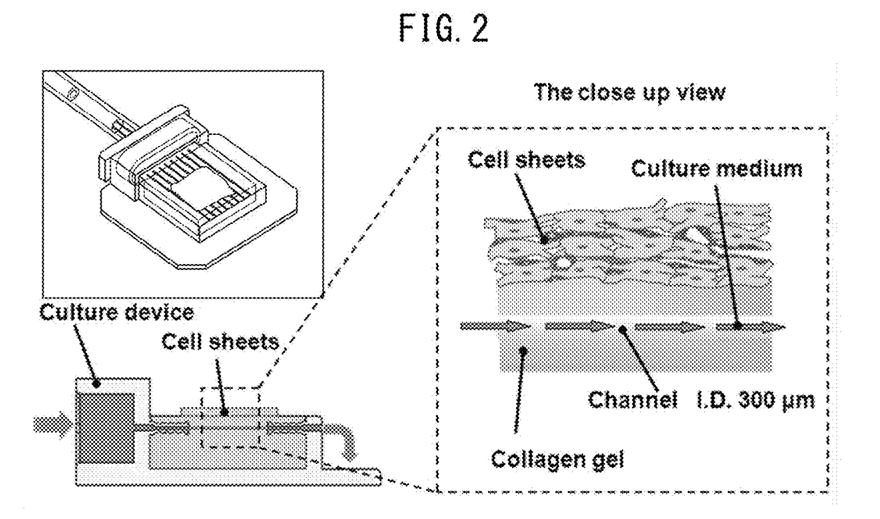
FIG. 2 is a diagram showing the outline of fabrication of the vascular bed of Example 1.
Figure 3:
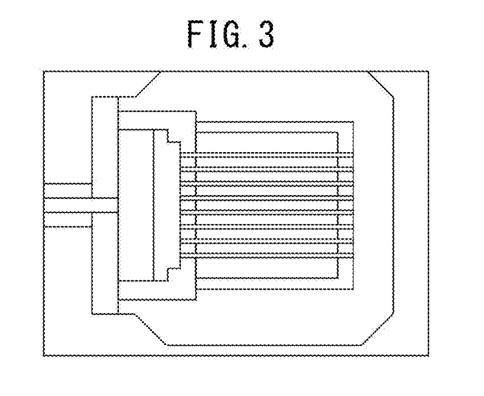
FIG. 3 is a diagram showing the outline of fabrication of the vascular bed of Example 1.
Figure 4:
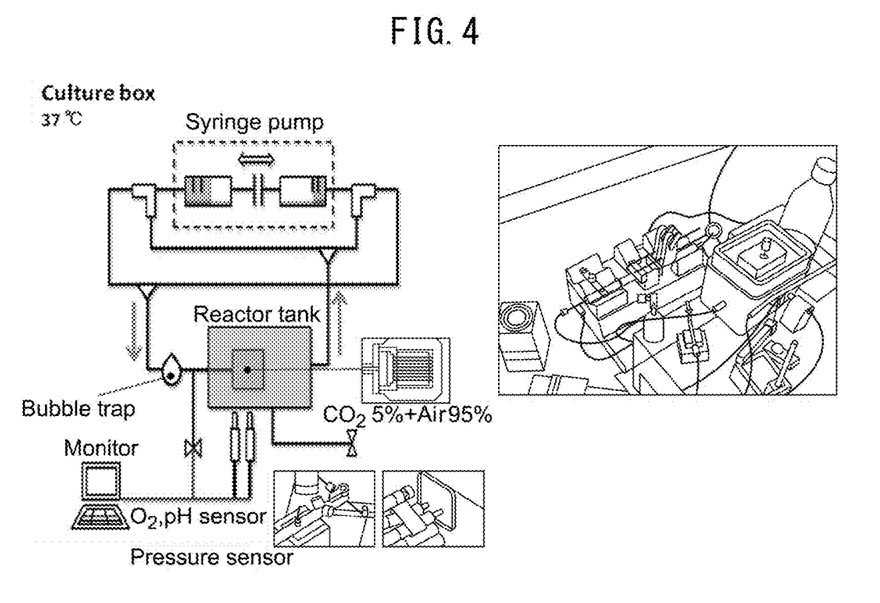
FIG. 4 is a diagram showing the outline of an apparatus for perfusing a medium to the vascular bed of Example 1.

As shown in FIG. 1, a stainless steel wire was provided on an acrylic frame, and into the frame, a collagen gel solution was run, cured and gelled. Then, the stainless steel wire was removed to obtain a gel having a microchannel. E of FIG. 1 shows the photograph of a corresponding apparatus, and FIG. 2 shows a schematic diagram explaining a method for constructing a vascular network inside the cell sheet using the apparatus. FIG. 3 snows a diagram in which a channel has been formed with the collagen gel. Also, a schematic diagram (left) of the outline of an apparatus for perfusing the culture medium into the collagen gel and a photograph (right) of an example of the apparatus are shown in FIG. 4. The arrow indicated in FIG. 4 (left) shows the direction in which the culture medium flows.

(Layering of a Cell Sheet on the Collagen Gel)

A multitude of cell sheets were layered and were allowed to adhere to the collagen gel. In a specific method, 2-6 layers of myocardial cell sheets was suspended on a culture dish, and after the culture medium was taken in and out with a piped aid to layer the sheets on the culture tray at one time, it was incubated for 30 minutes so as to be adhered and integrated. Then, it was adhered onto the collagen gel. In a perfusion culture bioreactor shown in FIG. 5 (right), the multilayered cell sheet layered on a vascular bed was cultured by perfusing the culture medium, from the channel while immersing it in the culture medium.

(Neovascular Formation in between the Cell Sheet and the Collagen Gel Vascular Bed)

Figure 5:
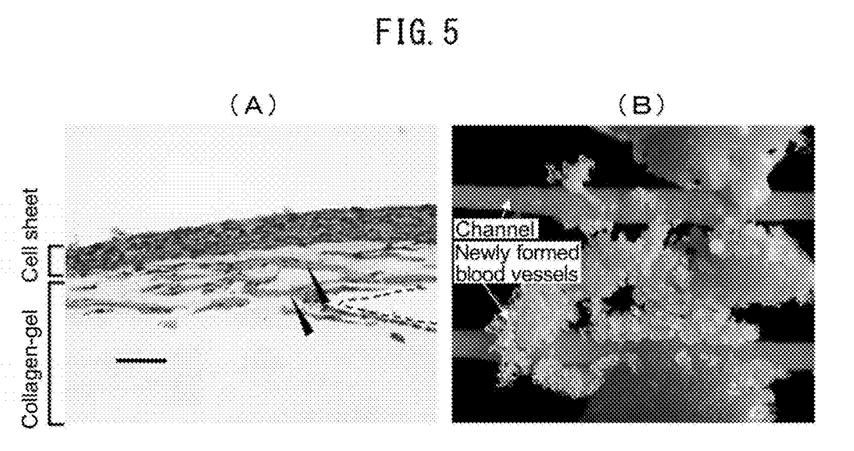
FIG. 5 is a diagram showing how vascular endothelial cells migrate toward the channel of the vascular bed. (A) shows a sectional view of a multilayered cell sheet, A region indicated by a dotted line shows a channel in the collagen gel, and the arrowhead indicates a capillary vascular network formed by the migration of vascular endothelial cells from the cell sheet. (B) shows that an acrylic resin was run in from the channel, and after curing, the gel and the cell sheet were removed.

When the cell sheet was perfusion-cultured on the vascular bed, vascular endothelial cells contained in the cells isolated from the rat's heart migrated toward the channel, thereby forming a capillary vascular network in between the vascular bed and the cell sheet (FIG. 5A). An acrylic subject was run into the channel and cured to observe neovascular formation. The result revealed the formation of numerous capillary vascular networks in between the vascular bed and the cell sheet (FIG. 5B).

(Pressurized Perfusion-Culture of the Cell Sheet on the Collagen Gel Vascular Bed)

As the number of layers of a cell sheet increases, the amount of oxygen required for cell metabolism increases. Thus, in order to increase the amount of dissolved oxygen to be perfusion cultured, an apparatus equipped with a mechanism for applying pressure on a sealed container for providing a vascular bed was added, and a pressurized perfusion-culture was performed according to the method described above. When a pressure of 20 mmHg was applied, compared to a culture without any such pressurizing, the amount of dissolved oxygen in the culture medium increased and vascular network construction in the cell sheet and vascular network formation in between the vascular bed and the multilayered cell sheet were promoted (data not shown). In the subsequent experiments, culturing was performed at a pressure of 20 mmHg.

(Method for Layering at One Time)

Figure 6:
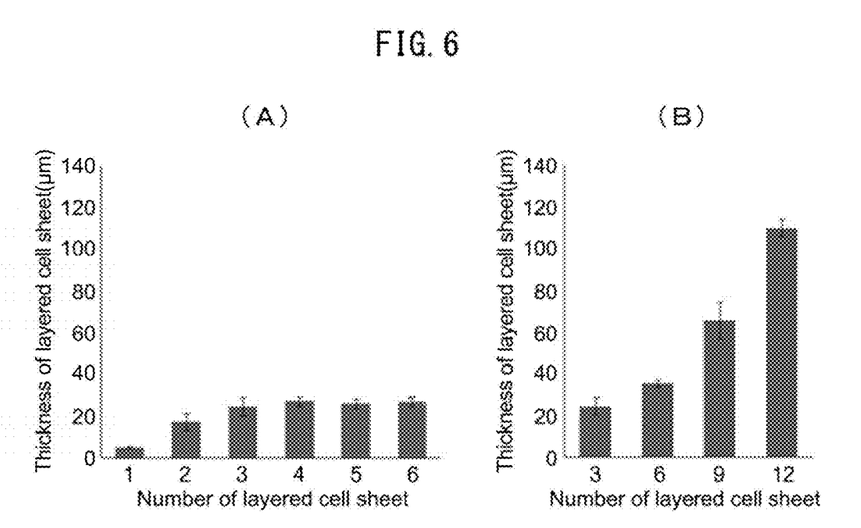
FIG. 6 is a diagram showing the thickness of the multilayered cell sheet of Example 1. (A) is a diagram showing the number (abscissa) of sheets layered at one run and the thickness (ordinate) of the cell sheet after perfusion culture. (B) is a diagram showing the thickness of a cell sheet formed by layering three cell sheets on a vascular bed, perfusion-culturing for a given period of time, then layering three cell sheets again, and repeating the procedure. The abscissa indicates the relationship between the numbers of cell sheets layered, the number of layering, and the thickness.

After the cell sheet was perfusion cultured for 5 days on the collagen gel vascular bed, the layered myocardial cell sheet-attached collagen gel was removed from the perfusion apparatus. After tissue-staining the gel in 4% paraformaldehyde, it was excised in sections in paraffin. The cross-sectional image of each layer observed by HE staining of the paraffin section is shown in FIG. 5(A). The dark arrowhead shown in FIG. 5(A) indicates a capillary vessel formed by the migration of vascular endothelial cells contained in the cell sheet toward the channel in the vascular bed of the gel. FIG. 5(B) shows that an acrylic resin was run into the channel of the gel, and after curing, the gel and the cell sheet were removed. In the method of measuring the thickness of tissue in each layer, the HE stain image was digitized and the thickness at 10 sites was measured. As a result, the thickness of second and third layers increased as the number of layers increased, whereas for a 4th layer or more, no changes in the thickness were noted. The measured values were about 7 μm for the first layer, about 18 μm for the second layer, about 24 μm for the 3rd layer, about 23 μm for the 4th layer, about 26 μm for the 5th layer, and about 23 μm for the 6th layer. Thus while the thickness of the tissue increased as the number of layers increased up to the third layer, the thickness of layers greater than the third layer was almost equal to that of the third layer (FIG. 6A). The reason for this may be that the supply of oxygen and nutrients and the removal of wastes due to diffusion in the cell sheet may reach only up to the third layer, and thus the cell sheet on the 4th layer or more may become necrotic.

(Multistage-Stacking Method)

Figure 7:
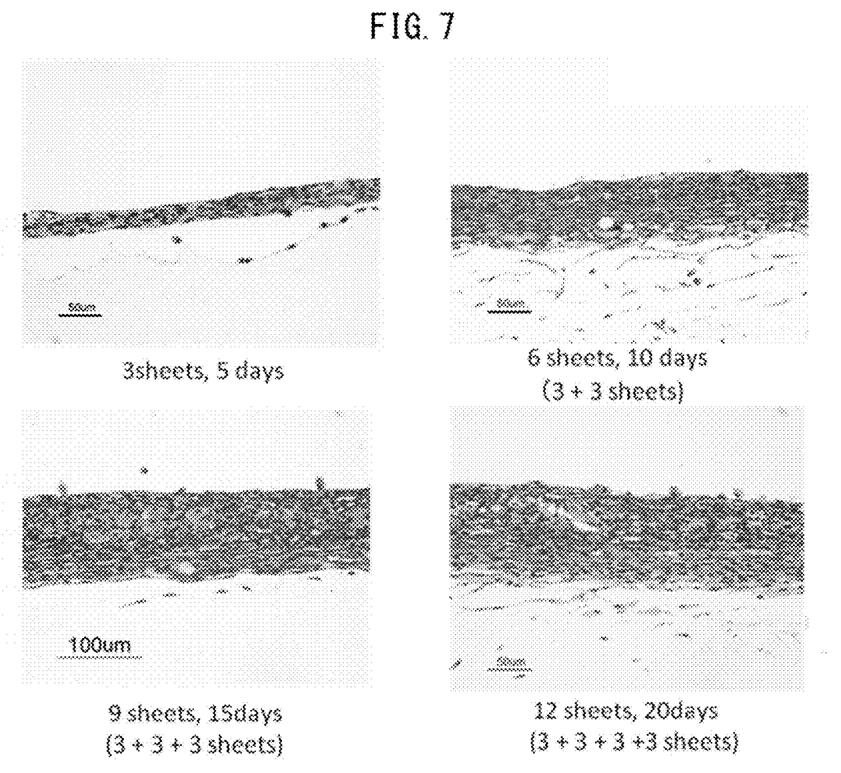
FIG. 7 is a diagram showing the relationship between the number of layering and the thickness of cell sheets of Example 1.

Thus, it was devised to repeat layering after a vascular network was formed by an artificial channel in the collagen gel and the cell sheet. Since the myocardial cell sheet of the primary isolate contains fibroblasts, endothelial cells, and smooth muscles in addition to myocardial cells, neovascular formation is expected to occur by the presence of blood vessels in the cell sheet and by performing a gel culture. Thus, it was assumed that by preparing a channel for perfusing a culture medium into the collagen gel and culturing the myocardial cell sheet of the primary isolate on the collagen gel channel, a fresh culture medium could be supplied to the myocardial cells even in a thick tissue if blood vessels are newly formed from the cell sheet and connected to the artificial channel. Thus, after a blood vessel was constructed, repeat layering of the cell sheet was performed. Considering the fact that the limit number of layers constructed at one time during perfusion culturing was three layers from the above experiment, and that it took five days before vascular networks were constructed in between the artificial channel and the cell sheet and connected, repeat experiment was performed. The results are shown in FIG. 6. Specifically, layering was repeated with the number of layers being three or less at an interval of five days. Here, the thicknesses of tissues prepared by: (1) culturing 6 layers (3 layers+3 layers) for a total of 10 days, (2) perfusion culturing 8 layers (3 layers+3 layers+2 layers) for a total of 15 days, and (3) perfusion culturing 9 layers (3 layers+3 layers+3 layers) for a total of 15 days were compared to a tissue prepared by single layering (3 layers, 5 days) to see changes in thickness. After culturing, the sample was fixed in 4% paraformaldehyde, and the paraffin sections were HE-stained. Each of the stained tissues is shown in FIG. 7. 3 layers+3 layers+3 layers were repeatedly layered with an interval culturing period of 5 days for a total of 15 days. As a result, a thickness of 78±11 μm was observed. After 3 layers+3 layers+3 layers were perfusion cultured for 15 days, the 9 layers did not necrotize and maintained the thickness of 115±10 μm. Since this thickness exceeds the limit thickness of oxygen and nutrient supply by diffusion from the surface, this demonstrated the effectiveness of the method of repeatedly layering cell sheets after the blood vessel was constructed and the culture medium was supplied upward. It was shown that by using the culturing apparatus of the present experiment, a transplantable tissue can be constructed.

Example 2

Method of Preparing a Gel Having a Channel Provided Therein

Figure 8:
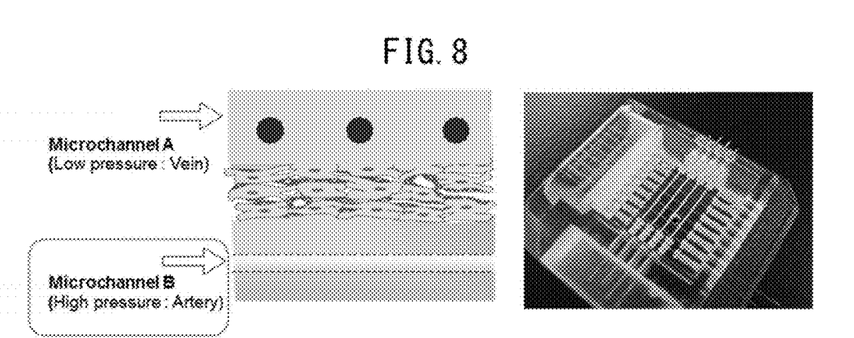
FIG. 8 is a diagram showing the outline of a vascular bed having channels on and under the multilayered cell sheet of Example 2.
Figure 9:
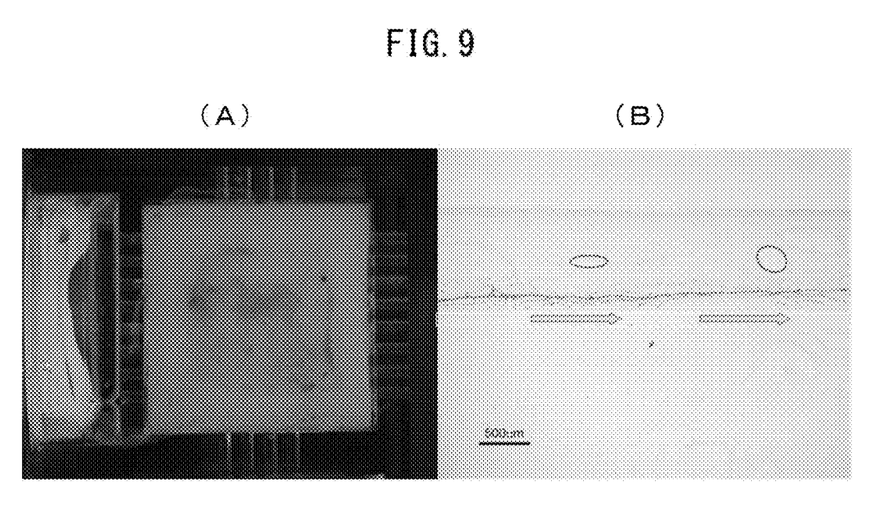
FIG. 9 is a diagram showing the outline of fabrication of a multilayered cell sheet on a vascular bed having channels on and under the multilayered cell sheet of Example 2. (A) shows a diagram when red blood cells were run from the channel, and (B) shows a diagram of the cross section of a multilayered cell sheet fabricated with a vascular bed having channels on and under the multilayered cell sheet.

As shown in FIG. 8, a vascular bed-forming container was fabricated that was designed to generate channels on and under the multilayered cell sheet. A stainless steel wire was provided on an acrylic frame, and into the frame, a collagen gel solution was run, cured and gelled. Then, the stainless steel wire at the lower part was removed to obtain a gel having a microchannel. Thereafter a three-layer myocardial cell sheet was layered. Then, at the upper part of the multilayered cell sheet, a stainless steel wire was mounted, and into the frame, a collagen gel solution was run and gelled. Then, the stainless steel wire at the upper part was removed to generate a channel at the upper part as well. In this experiment, culturing was performed at a flow rate of the lower channel of 500 μl/min (FIG. 8 (left), Microchannel A) and a flow rate of the upper channel of 250 μl/min (FIG. 8 (left), Microchannel B), and a perfusion culture was performed for 5 days in the bioreactor shown in FIG. 4. After the perfusion culture, blood was perfused from the lower channel in order to confirm the connection of the capillary vascular network in the cell sheet and the channel in the vascular bed (FIG. 9A). As a result, the color of the upper part of the cell sheet was found to be changed, indicating that a channel has been formed in between the gel and the multilayered cell sheet. Furthermore, blood vessel-like structures formed in the upper and the lower channels were confirmed (FIG. 9B). The result confirmed that vascular endothelial cells migrated toward the lower channel where the flow rate is faster, forming a vascular network (FIG. 9B). When the upper and the lower flow rates of the multilayered cell sheet were reversed, vascular endothelial cells migrated toward the upper channel where the flow rate is faster. This suggested that in vascular network construction by vascular endothelial cells, the vascular network is constructed by the effect of the physical characteristics of the flow rate of the culture medium. Furthermore, when the distance between the cell sheet and the channel is 100 µm or less, vascular endothelial cells migrate efficiently, and blood vessel-like structures are formed.

(Neovascular Formation Model of Multilayered Cell Sheet)

Figure 10:
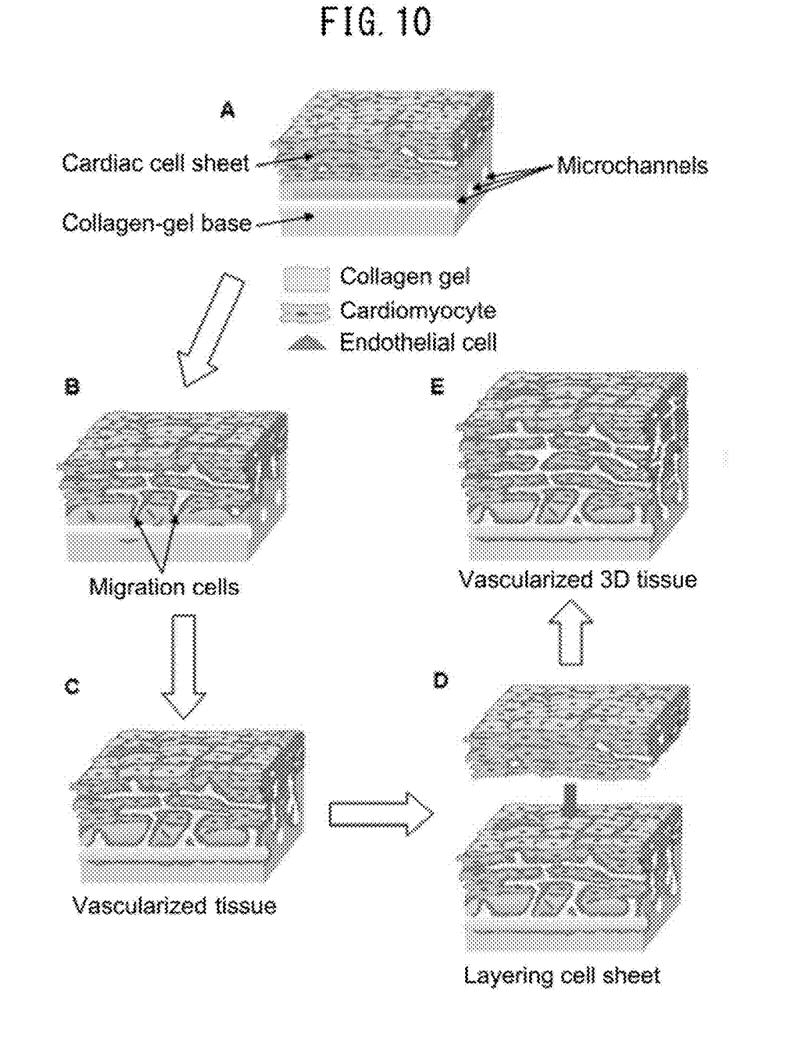
FIG. 10 is a diagram showing the outline of fabrication of a multilayered cell sheet on the vascular bed of Example 1 and Example 2.

FIG. 10 is a diagram showing the outline of vascular network construction induced during the fabrication of a multilayered cell sheet using a vascular bed. From a cell sheet (FIG. 10A) placed on the collagen gel, vascular endothelial cells migrate toward the channel (FIG. 10B), and coat the inner wall of the channel, forming a lumen structure (FIG. 10C). Thereafter, further transplantation of the multilayered cell sheet on the upper layer (FIG. 10D) causes the connection of the lumen structure connected to the gel channel and the vascular endothelial cells in the newly layered cell sheet, leading to vascular formation (FIG. 10E). By repeating this process, a thick multilayered cell sheet can be fabricated (FIG. 10E).

INDUSTRIAL APPLICABILITY

In accordance with the production method of the present invention, a vascular network can be constructed in a cell sheet, and by layering the sheet, a thick multilayered cell sheet can be easily fabricated. Such a thick multilayered cell sheet is useful as an in-vivo tissue substitute in regenerative medicine for various tissues.

The invention claimed is:

1. A method for producing a cell sheet construct comprising a vascular bed and a multilayered cell sheet layered on the vascular bed, said method comprises:
   (i) providing a channel in a gel for perfusing a culture medium to the surface of the gel,
   (ii) adhering a cell sheet containing vascular endothelial cells on the surface of the gel to induce vascular endothelial cells into the gel,
   (iii) perfusing the culture medium through the channel to generate a vascular bed having a vascular network constructed in the gel and on the surface of the gel, and
   (iv) layering cell sheets of two or three layers for a plurality of times on the vascular bed to construct a vascular network in the multilayered cell sheet having vascular endothelial cells of the cell sheets arranged towards the channel in the gel,
   wherein the cell sheet is obtained by culturing cells on a cell culture support coated with a polymer and in the culture medium at a temperature ranging from 0-80° C. such that the polymer has a weak hydration force, and detaching the cultured cells in a sheet form by changing the temperature of the culture medium such that the polymer has a strong hydration force, and wherein the cell sheet construct has the vascular network constructed between the multilayered cell sheet and the channel in the gel, and wherein the cell sheet construct comprises five layers or more of the cell sheet.

2. The method according to claim 1, wherein the gel comprises a biodegradable polymer and/or a cell.

3. The method according to claim 2, wherein the biodegradable polymer is a collagen gel and/or a fibrin gel.

4. The method according to claim 1, wherein the vascular bed in which the cell sheet was layered has been immersed in a culture medium in a sealed container that can maintain a constant temperature and atmosphere.

5. The method according to claim 4, wherein the inside of the sealed container has been pressurized.

6. The method according to claim 1, wherein the culture medium contains hepatocyte growth factor (HGF), fibroblast growth factor (FGF), epidermal growth factor (EGF), platelet-derived growth factor (PDGF), insulin-like growth factor (IGF), angiopoietin, transforming growth factor-β (TGF-β), placental growth factor (PlGF), matrix metalloproteinase, or family proteins of the above-mentioned factors to enhance capillary vessel density in the multilayered cell sheet and in between the multilayered cell sheet and the vascular bed.

7. The method according to claim 1, wherein the polymer, of which hydration force varies in the temperature range of 0-80° C., is poly(N-isopropylacrylamide).

8. The method according to claim 1, wherein the method comprises layering the upper surfaces of two cell sheets with each other.

9. The method according to claim 1, wherein the method comprises layering a gel having a channel provided therein on a cell sheet that has been layered on the vascular bed, and the space between the cell sheet and the channel was set as a distance of 100 µm or less.

10. The method according to claim 9, wherein a flow rate of the culture medium to be perfused is different at the upper and lower channels of the multilayered cell sheet.

* * * * *